(12) United States Patent
Rozental et al.

(10) Patent No.: US 10,076,248 B2
(45) Date of Patent: Sep. 18, 2018

(54) HYBRID CATHETER SYSTEM

(71) Applicants: Amir Rozental, Haifa (IL); Farouc Jaffer, Jamaica Plain, MA (US); Vasilis Ntziachristos, Grafelfin (DE); R. Nika Mendelev (Nudelman), Munich (DE)

(72) Inventors: Amir Rozental, Haifa (IL); Farouc Jaffer, Jamaica Plain, MA (US); Vasilis Ntziachristos, Grafelfin (DE); R. Nika Mendelev (Nudelman), Munich (DE)

(73) Assignee: The General Hospital Corporation, Boston, MA (US)

( * ) Notice: Subject to any disclaimer, the term of this patent is extended or adjusted under 35 U.S.C. 154(b) by 463 days.

(21) Appl. No.: 14/437,765

(22) PCT Filed: Oct. 18, 2013

(86) PCT No.: PCT/US2013/065589
§ 371 (c)(1),
(2) Date: Apr. 22, 2015

(87) PCT Pub. No.: WO2014/066150
PCT Pub. Date: May 1, 2014

(65) Prior Publication Data
US 2015/0272445 A1    Oct. 1, 2015

Related U.S. Application Data

(60) Provisional application No. 61/716,881, filed on Oct. 22, 2012, provisional application No. 61/755,057, filed on Jan. 22, 2013.

(51) Int. Cl.
*A61B 5/00*    (2006.01)
*A61B 1/00*    (2006.01)
(Continued)

(52) U.S. Cl.
CPC .......... *A61B 5/0095* (2013.01); *A61B 1/0011* (2013.01); *A61B 1/00071* (2013.01); (Continued)

(58) Field of Classification Search
CPC .............. A61B 1/00071; A61B 1/0011; A61B 1/00165; A61B 1/043; A61B 1/07; (Continued)

(56) References Cited

U.S. PATENT DOCUMENTS

| 6,575,965 B1 | 6/2003 | Fitch et al. |
| 2002/0013529 A1 | 1/2002 | Smith et al. |
| 2009/0043191 A1* | 2/2009 | Castella ............... A61B 5/0066 600/425 |

OTHER PUBLICATIONS

The International Search Report and Written Opinion dated Mar. 20, 2014 for International Application PCT/US2013/065589.
(Continued)

*Primary Examiner* — Michael Rozanski
(74) *Attorney, Agent, or Firm* — Quarles & Brady LLP; Yakov Sidorin

(57) ABSTRACT

System and method for obtaining information about a target structure. The system includes an optoelectrical element with an optical fiber having a core, a coating surrounding the core, an optical axis, a proximal end, and a distal end. The optoelectrical element also includes an electrical connector embedded within the coating along the optical axis between the proximal end and the distal end. A transducer is disposed at the distal end and electrically connected to the electrical connector. The transducer is operable to detect a first energy, generated in response to light that has been transmitted from the proximal end to the distal end and outcoupled from the distal end toward the target structure, and to convert the received first energy to an electrical signal to be transmitted along the electrical connector.

19 Claims, 4 Drawing Sheets

(51) Int. Cl.
*A61B 1/04* (2006.01)
*A61B 8/12* (2006.01)
*A61B 8/00* (2006.01)
*A61B 1/07* (2006.01)

(52) U.S. Cl.
CPC ............ *A61B 1/043* (2013.01); *A61B 5/0071* (2013.01); *A61B 5/0084* (2013.01); *A61B 5/6852* (2013.01); *A61B 8/12* (2013.01); *A61B 8/445* (2013.01); *A61B 8/4416* (2013.01); A61B 1/00165 (2013.01); A61B 1/07 (2013.01); A61B 2562/0204 (2013.01); A61B 2562/0238 (2013.01)

(58) Field of Classification Search
CPC .... A61B 2562/0204; A61B 2562/0238; A61B 5/0071; A61B 5/0084; A61B 5/0095; A61B 5/6852; A61B 8/12; A61B 8/4416; A61B 8/445
See application file for complete search history.

(56) References Cited

OTHER PUBLICATIONS

Razansky, Nika R. et al, Double-cladding-fiber-based detection system for intravascular mapping of fluorescent molecular probes. Progress in biomedical optics and imaging, 2011, vol. 12, No. 12, abstract.

* cited by examiner

HYBRID CATHETER SYSTEM

CROSS-REFERENCE TO RELATED APPLICATIONS

The present application represents the national stage entry of PCT International Application No. PCT/US2013/065589 filed on Oct. 18, 2013 and claims priority from and benefit of U.S. Provisional Patent Applications No. 61/716,881 filed on Oct. 22, 2012 and titled "Hybrid Fluorescence-Optoacoustic Catheter"; and 61/755,057 filed on Jan. 22, 2013 and titled "Hybrid Catheter System". The disclosure of each of the above-identified patent applications is incorporated herein by reference in its entirety.

TECHNICAL FIELD

The present invention relates generally to systems and methods for medical imaging and, more specifically, to systems and methods adapted to simultaneously acquire, through complementary channels of different imaging modalities, data representing structural and functional tissue information.

BACKGROUND OF THE INVENTION

Optical imaging, such as fluorescence or optoacoustic imaging, can be used for in vivo imaging of molecular functions and gene expression in live biological tissues. For example, using externally administered agents with sensitivity and specificity to certain functional, molecular, and/or cellular targets (such as fluorochromes or nanoparticles), optical imaging can be used to visualize events that are not detectable using conventional imaging modalities, such as ultrasound or X-ray. Furthermore, the combination of these agents with an appropriate optical detection system can lead to very high detection sensitivity and high biological specificity. As a result, optical imaging approaches are becoming increasingly important for the diagnosis and monitoring of disease.

With respect to fluorescence imaging, generally, excitation light is transmitted toward a tissue to excite the emission of fluorescent light from fluorochromes associated with the tissue. This method is conventionally performed in fluorescence microscopy for high-resolution imaging of histological sections of biological tissue. In addition to this conventional use, examples of in vivo fluorescence imaging approaches include confocal imaging, multiphoton imaging, and total internal reflection fluorescence microscopy. The excitation light often used in these approaches is in the near infrared (near-IR) range, as higher tissue penetration depths can be achieved in comparison to those when light in the visible wavelength range is used. However, even using near-IR light, the in-tissue penetration limit of light during the fluorescence imaging is less than about 0.5 millimeters. As a result, in their current implementation, the fluorescence imaging systems are not appropriate for three-dimensional or quantitative imaging of hollow organs, such as in intravascular, pulmonary/bronchoscopic, or gastro-intestinal imaging.

For example, near-IR fluorescence catheter systems have been developed for detecting distributions of fluorescence in tissues, including imaging of hollow organs such as the gastrointestinal tract, pulmonary system, and cardiovascular system. In their present form, such systems rely predominantly on surface information derived from fluorescence reflectance imaging, which provides a number of drawbacks. In particular, the fluorescence signal emanating from target fluorescent probes embedded in the wall of a hollow organ suffers from attenuation due to scattering and absorption in tissue and blood. This attenuation is generally exponentially dependent on the unknown distance of the probes from the catheter when the organ is filled with blood. Thus, fluorescence light emanating from untargeted probes that are closer to the catheter than the actual targeted probes may overshadow the true signal and lead to inaccurate quantification. An example of such a scenario is provided by a situation when the hollow organ is a blood vessel and a fluorescent dye is circulated through the blood stream. In this case, the entire fluorescent image may be saturated from the fluorescence signal within the blood and, therefore, will not indicate whether any fluorescent probe exists deeper in the blood vessel wall. Because of these limitations, fluorescence catheters, endoscopic systems, and angioscopic systems substantially lack the ability to provide quantitative three-dimensional or even two-dimensional information. This type of information may be critical in some cases to accurately map disease, quantify response to therapies, and/or geographically localize fluorescence signals within target pathology.

An alternative to fluorescence imaging is multi-spectral optoacoustic tomography ("MSOT"). MSOT is based on illuminating a tissue with transient laser light and creating pressure variations inside the tissue through a thermo-elastic effect, which leads to acoustic wave propagation. These acoustic waves are conventionally measured at a distance from an inner or outer boundary of the tissue and used to form an image of the energy deposition within the tissue. By using laser light at different wavelengths, a three-dimensional map of tissue constituents and tissue biomarkers can be obtained. This technique has been shown to facilitate the differentiation of various tissue types according to their spectral properties and to image fluorescent probes and nanoparticles that exhibit an absorption resonance in the exciting wavelength. The advantage of this technique over the fluorescence imaging is that it can provide high resolution three-dimensional maps of the concentration of photoabsorbing agents. The ability to localize specific optical agents and tissue constituents in three dimensions enables the differentiation between different probes and tissues in a target region. Additionally, since the anatomy of the imaged tissue and a hollow organ space can be resolved with high resolution, a correction for light attenuation may be performed, leading to the improved quantitative spatial mapping of an agent and concentration of its specific biomarker. Thus, this technique can potentially overcome limitations of fluorescence imaging, namely undesired surface-weighted images and non-quantified results.

Conversely, in comparison to fluorescence imaging, optoacoustic imaging is less sensitive in detecting fluorochromes. This elicits a diagnostic limitation of stand-alone optoacoustic approaches. Although the detection sensitivity may be improved by, for example, including more exciting wavelengths or increasing the signal-to-noise ratio ("SNR") using averaging, these processes are associated with increased measurement time. While three-dimensional imaging requires hundreds to thousands of slices for proper assessment through visualization, the time required for measurement should ideally not be more than a few minutes for procedures such as intraluminal imaging due to their invasive nature. Furthermore, current approaches for increasing SNR in non-invasive MSOT methods cannot be translated to imaging of hollow organs. For example, non-invasive approaches have been demonstrated for two-dimensional imaging with measurement durations of a few seconds by utilizing multiple detectors and maximizing detector size. However, imaging of hollow organs poses very stringent restrictions on these characteristics. In particular, externally located detectors (that is, on the outside of the vessel) are not feasible for minimally invasive detection, and noninvasive sensors on the outside of the body are unlikely to detect a signal from an intravascular source without severe degradation of the signal. In addition, the sensor size is limited and multiplexing more than one sensor is complex and leads to the reduced SNR per sensor. Some attempts have been made for constructing an intravascular optoacoustic catheter by mounting an intra-vascular ultrasound ("IVUS") catheter on a thick optical fiber. The sensitivity and speed achieved with this catheter, however, were not sufficient for imaging molecular probes in vivo. Additionally, the total thickness of this two-shaft catheter was a few millimeters, preventing its safe use in human coronary-artery imaging.

Other approaches to improve fluorescence imaging of hollow organs have included the incorporation of optical coherence tomography ("OCT"). Currently, such approaches provide a dual-shaft catheter including a first shaft to perform fluorescence imaging and a second shaft to perform OCT, therefore providing functional information gathered through fluorescence imaging in combination with structural information gathered through OCT. As discussed above, two-shaft catheters require dimensions that are too large for safe use in many intraluminal applications, such as human coronary-artery imaging.

It would therefore be desirable to provide a method and system that is capable of both structural and functional imaging and is also dimensioned to safely perform such imaging for intraluminal applications.

SUMMARY OF THE INVENTION

The present invention overcomes the aforementioned drawbacks by providing a hybrid catheter system for intraluminal imaging that is operationally capable to generate tissue images representative of functional, structural, and/or molecular activity associated with the tissue. This is accomplished through multiple modes of imaging, including optical, optoacoustic, and/or acoustic imaging, via a single-shaft catheter design dimensioned to allow intraluminal navigation.

In accordance with one implementation of the invention, a system structured to obtain information of a target structure includes an optoelectrical element and a transducer. The optoelectrical element includes an optical fiber having a core, a coating surrounding the core, an optical axis, a proximal end, and a distal end, and operable to transmit light between the proximal end and the distal end. The optoelectrical element also includes an electrical connector embedded within the coating along the optical axis between the proximal end and the distal end. The transducer is disposed at the distal end and electrically connected to the electrical connector. The transducer is structured to detect a first energy, generated in response to light that has been transmitted from the proximal end to the distal end and outcoupled from the distal end toward the target structure, and to convert the received first energy to an electrical signal to be transmitted along the electrical connector. In one implementation, the first energy may include acoustic energy. Additionally, the system may include an optical coupling unit positioned between the distal end and the transducer and rotatable about the optical axis. Optionally, the optical coupling unit and the transducer are structurally cooperated with one another to ensure the simultaneous rotatability of the optical coupling unit and the transducer about the optical axis. Additionally or in the alternative, the optical coupling unit may be structured to be operable to receive a second energy that includes optical energy at a wavelength different from a wavelength of light outcoupled from the distal end towards the target structure and/or the optoelectrical element is configured as a single-shaft catheter dimensioned to be insertable into a lumen. Alternatively or in addition, the system may include a light source coupled with the proximal end and operable to generate light at a frequency defined to cause the target structure to generate the first energy receivable by the transducer in response to being illuminated with such light. The system may also include image data processing circuitry operably connected with the optoelectrical element through a rotary joint at the proximal end.

Embodiments of the invention additionally provide a method for imaging a target structure includes transmitting optical energy at a first wavelength toward the target structure using an optoelectrical element comprising an optical fiber and an electrically conducting member embedded within a coating of the optical fiber. The method also includes simultaneously acquiring both optical energy at a second wavelength from the target structure and acoustic energy from the target structure in response to the transmitted optical energy at the first wavelength. The method further includes transmitting the optical energy at the second wavelength through the optical fiber and/or transmitting the acoustic energy through the electrically conducting member to an image data processing system to form data representing the target structure. Alternatively or in addition, the method may include a step of generating an image of the target structure based on the optical energy transmitted at the second wavelength and the acoustic energy. The method may additionally include (i) transmitting an acoustic excitation signal towards the target structure through the optoelectrical element and (ii) acquiring acoustic energy, with the use optoelectrical element, from the target structure in response to the transmitted acoustic excitation signal received at the target structure.

In the following description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present invention provides a hybrid catheter system configured for functional, structural, and/or molecular imaging of target biological structures and relates to U.S. patent application Ser. No. 12/020,765 and 61/716,881. The disclosure of each of these applications is incorporated herein by reference in its entirety. The hybrid catheter system includes a single-shaft design structured to enable multiple imaging capabilities including optical imaging, optoacoustic imaging, and/or acoustic imaging. In addition, the single-shaft design is appropriately dimensioned for use in intraluminal imaging of hollow organs (such as angioscopic imaging applications, gastrointestinal imaging applications, bronchoscopic imaging applications, otorhinolaryngological applications, genitourinary imaging applications) and/or overall endoscopic and invasive imaging applications, where the employment of a catheter with more than one shaft is operationally impractical.

Figure 1A:
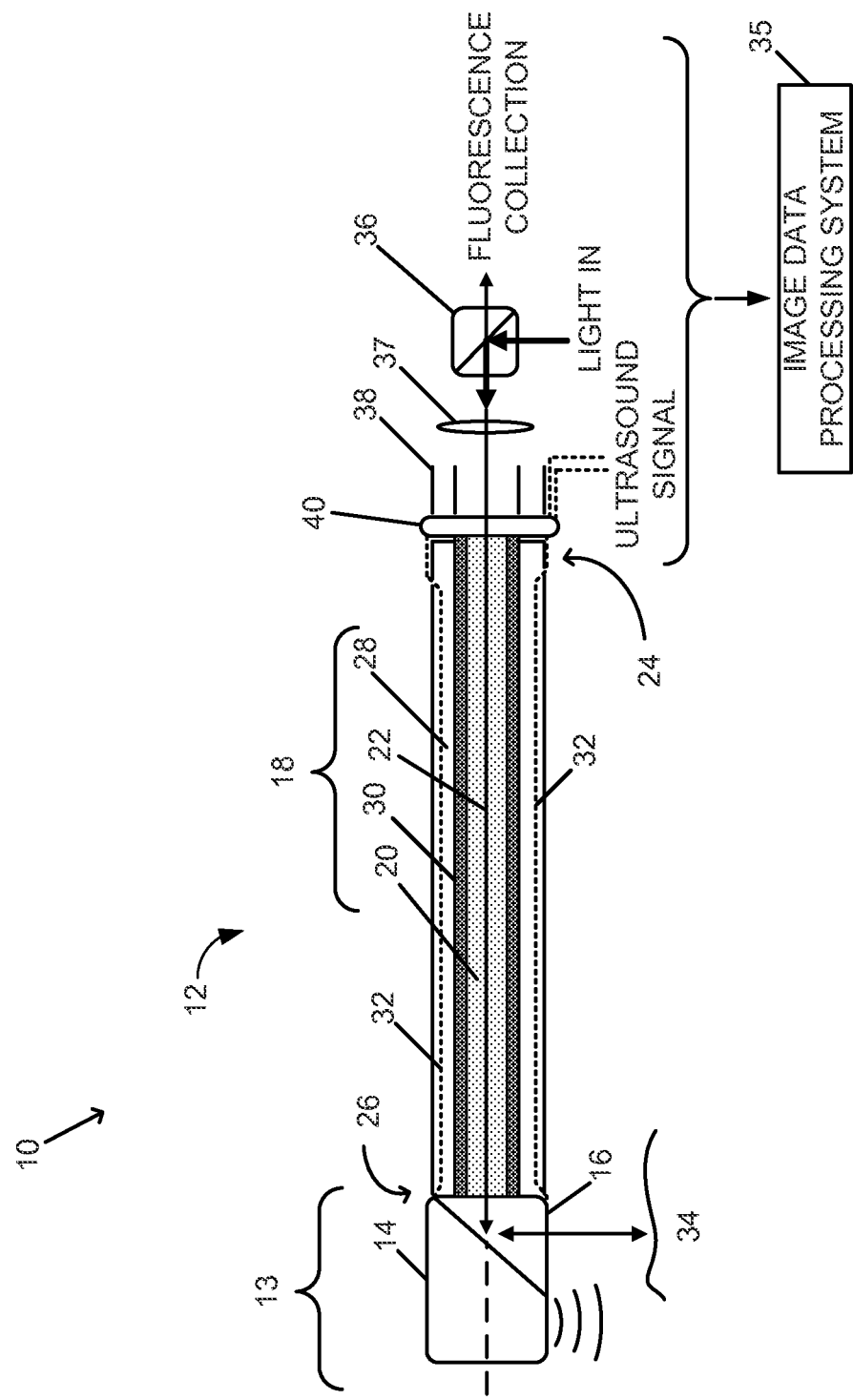
FIG. 1a is a side cross-sectional view of a hybrid catheter system according to present invention.
Figure 1B:
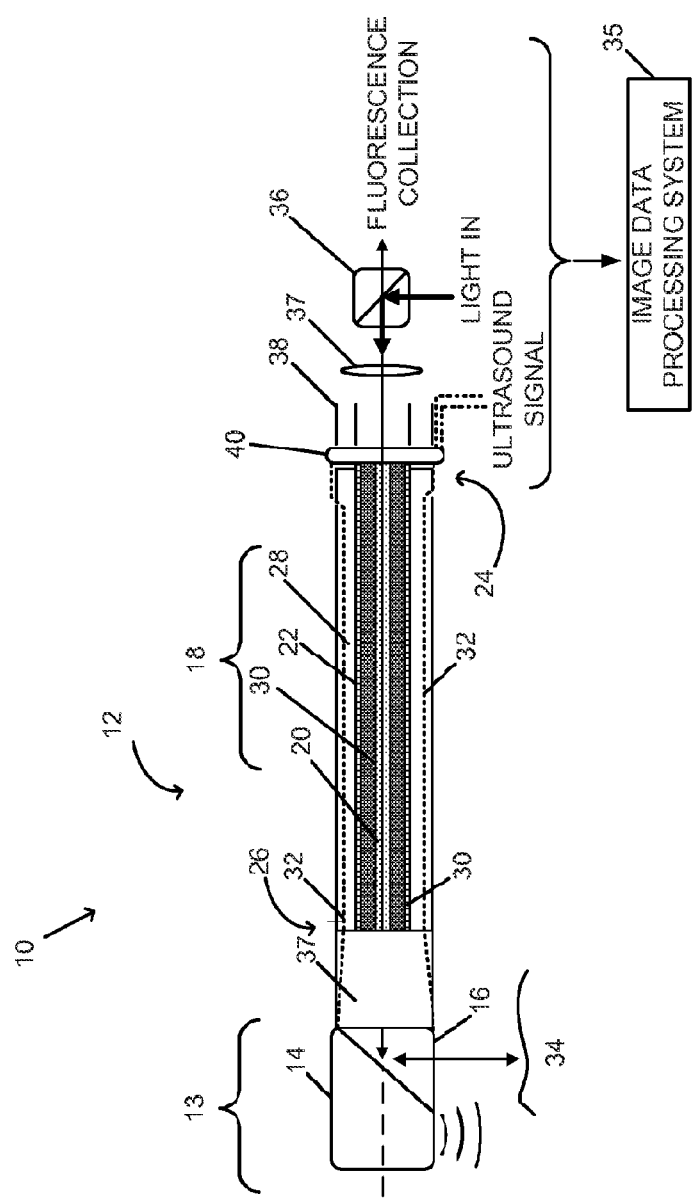
FIG. 1b is a side cross-sectional view of another hybrid catheter system according to present invention.

Referring to FIGS. 1a and 1b, embodiments of the hybrid catheter system 10 in accordance with the present invention are presented. As shown in FIGS. 1a and 1b, the hybrid catheter system 10 can include an optoelectrical element 12, and a probe unit 13 which, in one implementation, includes a transducer 14 and an optical coupling unit 16. The optoelectrical element 12 can include an optical light guide such as an optical fiber 18 (which label is not indicated in FIG. 1a, 1b) that includes a core 20, cladding 30, coating 28, and an optical axis 22; and proximal and distal ends 24, 26. The transducer 14 and the optical coupling unit 16 are in operable communication with the distal end 26 of the optoelectrical element 12. In different embodiments, the transducer 14, converting one form of energy into another, can be additionally configured as a transmitter, a receiver, and/or a transceiver. In addition, as shown in cross-sectional views of FIGS. 2a and 2b, embodiments 18A, 18B of the optical fiber can include coating(s) 28, 28A; an optional fiber cladding material 30; and one or more electrical connectors or members 32 embedded within the coating(s) 28, 28A as further described below. The electrical connector(s) 32, such as two wires, are in established electrical contact with the transceiver/transducer 14 and travel alongside the optical fiber 18 (that is, along the optical axis 22) from the distal end 26 to the proximal end 24, for example, to transmit an electrical signal from and to the transducer 14 along the optoelectrical element 12. In operation, the proximal end 24 can also be operably connected to an image data processing system 35 via a connecting module (not shown) to form an imaging system. Furthermore, optionally, a lens 37 may be provided between the probe unit 13 and the optoelectrical element 12, as shown in FIG. 1b.

As discussed above, and in contradistinction to catheters of the related art, the hybrid catheter system 10 is structured to enable optical imaging, optoacoustic imaging, and/or acoustic imaging with a single operable strand that cooperates a channel for electrical transfer of data with a channel for optical transfer of data. One or more of these imaging modes may be accomplished simultaneously or concomitantly by the hybrid catheter system 10 to provide co-registered images representative of functional, structural, or molecular activity of a target scene accessible through the transducer 14 and the optical coupling unit 16 (for example, a biological structure). To acquire optical data representative of the target scene, excitation light is delivered through the optical fiber 18 of the optoelectrical element 12 and outcoupled from the optical coupling element 16 toward a target biological structure 34, as shown in FIGS. 1a and 1b, and light received from the target biological structure 34 (for example, light emitted by the structure 34 in response to the incident excitation light) is collected by the optical coupling unit 16 and transmitted along the optoelectrical element 12 toward the proximal end 24 and further to the image data processing system 35. To accomplish acoustic imaging, an excitation electrical signal is transmitted along one or more electrical connectors 32 of the optoelectrical element 12 toward the transducer 14, converted to an acoustic signal and emitted toward the target biological structure 34, and responsive acoustic energy (that is, the acoustic energy returned in reflection by the target structure 34) is detected and converted to an electrical signal by the transducer 14, and further transmitted along the optoelectrical element 12 to the image data processing system 35. To accomplish optoacoustic imaging, excitation light is outcoupled from the optoelectrical element 12 and acoustic energy emitted from the target biological structure 34 in response to the excitation light incident thereon is detected, converted to an electrical and/or optical signal, and transmitted along the optoelectrical element 12 to the image data processing circuitry (such as a specifically-programmed computer processor, for example) of the system 35. More specifically, in an optoacoustic mode of operation, the structure 34 is illuminated with light delivered to the structure 34 along the optical fiber 18 and through the optical coupling unit 16. The delivered light creates pressure variations inside the tissue 34 through the thermo-plastic effect leading to an acoustic wave at the tissue 34. A portion of such acoustic wave detected at the transducer 14 is converted to electrical data that is delivered, along the electrically-conductive member(s) 32 to the image data processing system 35. Accordingly, these three imaging modes can be accomplished, unexpectedly, with the use of a single-strand optoelectrical element 12 juxtaposed the probe unit 13, thereby providing a single-shaft catheter design with dual- or tri-modal imaging capabilities.

With further reference to optical imaging, such as fluorescence imaging, excitation light from an optical source (such as a laser light source, not shown) can be transmitted through the optical fiber 18 from the proximal end 24 to the distal end 26 and outcoupled from the distal end 26 toward the target biological structure 34, such as tissue of a lumen. In one example, the excitation light is outcoupled from the distal end 26 in a direction that is substantially transverse to the optical axis 22. This is effectuated by employing, for example, an optical prism as part of the optical coupling unit 16 (as shown in FIG. 1a, 1b). Light emitted from the target biological structure 34 in response to the excitation light is collected by the optical fiber 18 through the same prism and transmitted from the distal end 26 to the proximal end 24. The detected light can then be transmitted to the image data processing circuitry (such as a specifically-programmed computer processor, for example) of the system 35 to form image data representing the target biological structure 34. This image data representing the target biological structure 34 may be used to generate an image of the target biological structure 34 and/or to extract or report (for example, make viewable to an operator or store on a tangible computer-readable medium) functional and/or molecular information of the target biological structure 34 (for example, of concentrations of targeted fluorescent probes in the target biological structure 34).

In an embodiment, the optical fiber 18 of the optoelectrical element 12 may include a single mode fiber or a multimode fiber with a single-clad design or a design including more than one fiber cladding, to name just a few. The hybrid catheter system 10 can be optically, through a beam-splitter 36 and a lens 37, juxtaposed with an optical detector component (such as a synchronized photon detector module, for example; not shown in FIG. 1a, 1b) that may be controlled by the image data processing system 35 or a separate controller of the imaging system. The optical detector component can include appropriate optical filters, for example to filter out light collected by the optoelectrical element 12 but that did not originate from fluorescent probes of the target biological structure 34.

In some applications, the hybrid catheter system 10 may be employed for multi-spectral fluorescence imaging. For example, excitation light at different wavelengths can be outcoupled from the optical coupling unit 16 to excite fluorescence associated with the target biological structure 34. For each excitation wavelength, fluorescence image data is collected and a corresponding fluorescence image can be generated. Factors that contribute to the differences between fluorescence images generated in response to excitation at different respective wavelengths can include: 1) the a priori known efficiency of a fluorescent probe (for example, a molecular/cellular targeted fluorochrome) at the given wavelength; 2) the scattering and absorption coefficients of the tissue or targeted fluorescent probe at the given wavelength; and 3) the distance of the fluorescent probe from the probe unit 13. As further discussed below, optoacoustic imaging can be performed to determine an absorption coefficient of the target tissue. Using this information and the fact that scattering is not strongly wavelength dependent, the distance between the fluorescent probe and the probe unit 13 may be determined. Thus, by employing several wavelengths for excitation, several fluorescent probes at different depths may be resolved. In the simplest form, the data processing operation could include a subtraction or division of data, but many other processing methods utilized in multi-spectral imaging can be applied. Such data processing may be executed by the image data processing system 35.

Furthermore, with respect to operation, the optical detector component may be optionally configured for light detection from a focal point or in a confocal detection, to enable the rejections of scattered light and optimal operation at a certain depth within the target biological structure 34. Accordingly, depth-dependent measurements can be effectuated by dynamically changing the position of an aperture and/or optical detector component with respect to the proximal end of the optoelectrical element 12. Multi-spectral imaging information may be further expanded with the use of a multi-spectral optical detector (such as a spectrograph, for example). A spectrograph can measure a spectrum of collected fluorescence light, therefore allowing two-dimensional spectral information to be obtained for each pixel in a generated fluorescence image. This information can be used to reduce the effect of auto-fluorescence in the hybrid catheter system. For example, some tissues, depending on their collagen levels, produce auto-fluorescence. Spectral analysis, through multi-spectral imaging, can permit the separation of sensed light due to desired probes fluorescing and sensed light due to auto-fluorescence. Normalizing optical information to remove auto-fluorescence (in other words, by only using sensed light from desired probes fluorescing), increased sensitivity and/or SNR may be achieved. This may be desirable when detecting anatomical features, or changes thereof, in generated images. Furthermore, determining the amount of auto-fluorescence sensed from a specific tissue may be helpful in certain diagnostic applications. Additionally, with respect to multi-spectral imaging, since different wavelengths of fluorescent light are attenuated differently, the additional spectral information may be used for better resolving the depth of the sensed fluorochromes.

With respect to image reconstruction and generation, for example via the image data processing circuitry of the system 35, one method to perform depth-resolved fluorescence reconstruction includes using a model-based optimization algorithm. Such a model can receive, as input, a three-dimensional map of optical absorption and scattering coefficients of the target biological structure medium 34, the location, concentration, and spectrum of the fluorescent probes, and the location and orientation of the optoelectrical element 12. The model can then output a fluorescence signal that is expected in actual detection. The scattering coefficient may assume an a priori distribution (for example, one value for blood and a different value for tissue), and the absorption coefficient can be obtained from optoacoustic images, as further discussed below. The absorption and fluorescence spectrum of the probes may also be a priori determined according to the known properties of the respective fluorescent probes. The model can then connect a map of a concentration of the fluorescent probes to the signal that should be measured or detected. The optimization algorithm may use methods such as random search, genetic algorithms, descent algorithms, etc. to determine a final fluorescent-probe map that outputs signals which best fit actual measured signals.

In addition to fluorescence imaging, other optical imaging modes can be applied using similar techniques as described above, such as optical coherence tomography (OCT), Raman spectroscopy, and/or NIR spectroscopy. In any event, the optical imaging mode of the hybrid catheter system 10 can generally provide a first light outcoupled toward the target biological structure 34 and detect a second light of a different wavelength, of the same wavelength, of different angles, etc. for use in generating an image of the target biological structure 34.

Referring now to optoacoustic imaging, excitation light from the optical source can be transmitted through the optical fiber 18 from the proximal end 24 to the distal end 26 and outcoupled from the distal end 26 toward the target biological structure 34. Acoustic energy emitted from the target biological structure 34 in response to the excitation light can be detected by the transducer 14, converted to an electrical signal, and transmitted from the distal end 26 to the proximal end 24 via the electrical connectors 32. This electrical signal can then be transmitted to the image data processing system 35, which can generate a three-dimensional image of the target biological structure 34 thereby providing structural information of the target biological structure 34. Furthermore, the data gathered can be processed to extract and/or report structural information of the target biological structure 34. Alternatively, in some applications, the transducer 14 can be connected to the optical fiber 18 and can convert the detected acoustic energy to an optical signal for transmission of the optical signal through the optical fiber 18 to the image data processing system 35.

The hybrid catheter system 10 can provide optoacoustic imaging using excitation light at a single wavelength or a set of wavelengths, thus enabling multi-spectral optoacoustic imaging, or multispectral optoacoustic tomography ("MSOT"). To enable clinically viable imaging rates, for example, the excitation light can be pulsed at substantially high rates (such as greater than 1 kHz or 10 kHz) or the excitation light can be intensity modulated with a complex periodic envelope at substantially high repetition rates (such as greater than 1 kHz or 10 kHz). A typical spectral range in which the excitation light is provided is from about 600 nanometers (nm) to about 1000 nm, however embodiments of the present invention may be configured to operate within other spectral windows (such as within the visible light range). Light at selected wavelengths within the chosen spectral range can be delivered to the target tissue 34 at different times, thereby providing acoustic signals proportional to the absorption at each respective wavelength. The acoustic signals for each given wavelength can be processed to generate an optoacoustic image of the energy absorbed in the tissue at the specific wavelength. The image may be further processed to obtain the absorption coefficient at the given wavelength. Thus, the multi-spectral images may be used to find the absorption spectrum throughout the depth of the imaged tissue. This spectral information may be used to determine the composition of the tissue/blood and also as prior knowledge for improving the quantification of fluorescence images, as discussed above. In addition, in some applications, MSOT may also be used to detect fluorescent probes in the target biological structure.

Referring now to acoustic imaging, such as ultrasound imaging, an electrical excitation signal can be transmitted, from the image data processing system 35 or a separate controller of the imaging system, across the electrical connectors 32 to the transducer 14. The electrical excitation signal is converted to an acoustic signal and the transducer 14, operating as a transceiver, emits the acoustic signal toward the target biological structure 34. Acoustic energy emitted from the target biological structure 34 in response to the acoustic signal can be detected by the transducer 14 and converted to an electrical signal, which is then transmitted from the distal end 26 to the proximal end 24 via the electrical connector(s) 32 and further to the image data processing system 35. The image data processing system 35 is enabled to generate an ultrasound image of the target biological structure 34 to provide three-dimensional structural information thereof. Furthermore, the data gathered can be processed to extract and/or report structural information of the target biological structure 34. Alternatively, in some applications, the transducer 14 can be connected to the optical fiber 18 and can convert the detected acoustic energy to an optical signal for transmission of the optical signal through the optical fiber 18 to the image data processing system 35.

As discussed above, the hybrid catheter system 10 can be dimensioned for use in intraluminal imaging. As a result, one specific application of the acoustic imaging mode can include intravascular ultrasound ("IVUS") imaging. More specifically, IVUS imaging can be performed by emitting an ultrasound burst from the transducer 14 (for example, via a pulse-echo operation) and detecting the waves reflected from the tissue back to the transducer 14. The data gathered from the reflected acoustic waves can be processed to form a three-dimensional structural image of the hollow organ, representing its acoustic properties.

The hybrid catheter system 10 can accomplish one, two, or three of the above-described imaging modes simultaneously, concurrently, or consecutively to accurately capture structural and/or functional features of the target biological structure 34. As discussed above, concurrent imaging (such as optoacoustic imaging at the same time as or overlapped by optical imaging) can enable information collected through one imaging mode (such as optoacoustic) to be used as a priori information when controlling another imaging mode (such as optical, and more specifically fluorescence). Such concurrent imaging, and in particular, enabling the use of a priori information obtained through optoacoustic imaging, can help improve conventional fluorescence imaging quantification issues associated with the strong non-linear dependence of fluorescence intensity on the depth of propagation. Thus, generally, the hybrid catheter system 10 can accomplish multiple imaging modes by emitting one form of energy (such as optical energy at a first wavelength) and detecting or measuring another form of energy (such as acoustic energy or optical energy at a second, different wavelength). In contrast, optical imaging with other hybrid catheters only allows for emission of optical energy at a first wavelength toward a biological structure and then detection of scattered photons at that same first wavelength. Furthermore, such catheters are limited in their ability to perform molecular imaging based on administrated contrast agents.

In one specific application example, the hybrid catheter system 10 can provide simultaneous dual fluorescence and optoacoustic imaging by detecting emitted fluorescent light and acoustic energy from the target biological structure 34 in response to the same excitation light outcoupled from the optoelectrical element 12. Accordingly, in such applications, the hybrid catheter system 10 can illuminate tissue at its distal end 26 and can detect energy of the same nature (light) and/or of a different physical nature (sound) created in the biological structure 34 as a result of the single illumination. In addition, in such applications, multiple time-shared laser excitations may also be feasible, in accordance with the present invention. In another example application, the hybrid catheter system 10 can combine optical and acoustic imaging, such as fluorescence and ultrasound imaging. Optoacoustic imaging may also be integrated, as well as other optical imaging modes, such as Raman spectroscopy, optical coherence tomography (OCT), and/or NIR spectroscopy. In applications that include both optoacoustic imaging and acoustic imaging (such as with dual optoacoustic and acoustic imaging or with triple optical, optoacoustic, and acoustic imaging), one imaging operation can follow the other imaging operation in a consecutive manner, rather than performing the operations simultaneously, in order to prevent cross talk between the two modes. In addition, in some applications, the hybrid catheter system 10 can provide multiple optical imaging modes, such as combined NIR Fluorescence imaging and OCT.

As described above, the hybrid catheter system 10 can be dimensioned for use in intraluminal imaging. For example, a diameter of less than or equal to about 1 millimeter can enable safe intraluminal navigation of the hybrid catheter system 10. During intraluminal imaging, the hybrid catheter system 10 is inserted into and moved along a lumen with the use of a push/pull means (not shown), while the probe 13 is activated to angularly rotate about the axis 22 to enable a capture of acoustic and/or optical information within a substantially 360-degree, or circumferential range (that is, transverse to the optical axis 22) within the hollow lumen. More specifically, the optical coupling unit 16 and the transducer 14 can be controlled to rotate, simultaneously or independently, about the optical axis 22 and relative to a stationary shaft portion 38 at the proximal end 24 (as shown in FIGS. 1a and 1b), for example continuously or at angular intervals, to enable 360-degree image capture (that is, a cylindrical view) of the hollow lumen via optical, optoacoustic, and/or acoustic imaging. To effectuate such repositioning and/or re-orientation of the probe 13 in some applications, an embodiment of the hybrid catheter 10 can comprise a rotary joint 40 including an optical rotary joint optionally integrated with an electrical rotary joint. For example, to enable electrical connections between the transducer 14 and the image data processing system 35, the electrical rotary joint may be implemented using slip rings centered on the optical rotary joint, thus providing a single, combined joint similar in configuration to rotary joints used for low-frequency power transmissions.

The simultaneous operation of multiple imaging modes, as well as the repositioning and angular re-orientation of the probe 13 of the catheter along a lumen, enables co-registration of multi-modal images to accomplish 360-degree image data capture along a length of the lumen. For example, the image data processing system 35 can determine and/or control rotation rate and pull-back movement of the catheter 10, executed by a processor of the image data processing system 35, in physical units (such as degrees and centimeters, respectively, over time). These physical measurements can then be co-registered with acquisition rates of the acquired acoustic energy and light delivered through the optoelectrical unit 12 and the rotary joint 40 of the catheter 10 from the target biological structure 34 and/or illumination rate of the light source in order to produce dimensionally accurate images. Using an appropriate computer-program product stored, for example, on a tangible computer-readable medium associated with the image data processing system 35, the image data processing system 35 is enabled to generate three-dimensional images of the lumen or two-dimensional representative images of such three-dimensional images.

Thus, the hybrid catheter system 10 can enable two- or three-dimensional, quantitative fluorescence imaging combined with optoacoustic and/or IVUS imaging of hollow organs by employing integrated imaging of the hollow structure architecture. Depth-resolved and optical property-corrected fluorescence imaging, using the techniques described above, integrated with single frequency or multi-spectral optoacoustic imaging and/or IVUS imaging can yield a wealth of information including accurate anatomical, functional and/or molecular information. In a specific example, such capabilities can greatly increase the clinical potential of the present invention as an intravascular catheter for in vivo detection of high-risk atherosclerotic lesions and evaluation of vascular stent pathology, as well as the progress of disease and treatment (for example through accurate co-registration of structure and disease biomarkers).

With further reference to the single-shaft design of the present invention, this design can be accomplished through the use of the single optical fiber 18 and the electrical connections 32 (such as micro-wires) embedded within the coating 28 of the optical fiber 18. Related implementations of hybrid optical-electrical catheters are based on two or more shafts or strands held next to one another in a single sheath, such as one or more shafts enabled for purely electrical operation and connected to an ultrasound transducer and one or more shafts adapted for purely optical operation. Double-shaft or double-strand designs have two major drawbacks compared to the single-shaft design of the present invention: size and complexity. In terms of size, because at least two shafts are used instead of one, and because of the extra sheath often necessary to hold these shafts as single unit, the size of the resulting catheter is larger than the sum of the sizes of the catheter's components. As a result, double-shaft catheter designs may be unsafe or incompatible for intraluminal imaging, where smaller dimensions are required for navigation through a biological lumen. In terms of complexity, the use of non-concentric geometries, in which both shafts are not rotating around their own axes, requires more sophisticated rotary joints to connect the rotating optical and electrical shaft to stationary shafts. Such rotary joints are often characterized by high optical losses. Conversely, because the center of rotation of the present system 10 is through the center of the optical fiber 18 (i.e., the optical axis 22), conventional concentric optical rotary joints may be optionally used at the proximal end 24 of the catheter 10 (such as that described in the U.S. Pat. No. 4,398,791, the entire contents of which are incorporated herein by reference) instead of complex, non-concentric optical rotary joints.

Moreover, conventional ultrasound intraluminal catheters (that is, not hybrid catheters) require coaxial cables to pass electric signals to and from transducers. This conventional approach is characterized by low losses of the transmitted signals. However, the use of wires, like that used in the present invention, is uncommon in ultrasound because their associated signal attenuation is significantly higher than that which is obtained in coaxial cables. For example, generally, when micro-wires are used, loss in signal may be expected owing to bending and resistive losses. Nonetheless, the signal attenuation in wires sized for the present invention (such as 50 micrometer-diameter wires) may be acceptable for the above-described uses of the present invention. For example, a feasibility experiment comparing micro-wires to coaxial cables illustrated that the use of micro-wires may lead to a loss of approximately 50 percent in signal amplitude. Specifically, coaxial signals were generated using a 15 MHz transducer with a coaxial cable connected to an ultrasound pulser/receiver. The arrangement was operated with a pulse-echo technique to measure the acoustic reflection from a carbon tube placed at a distance from the transducer. Micro-wire signals were then generated by replacing the coaxial cable with two wires that were 2 meters long and 50 micrometers in diameter. The same operation was performed and the acoustic reflection from the same target was measured. Although use of the wires resulted in a somewhat undesirable loss in signal attenuation compared to coaxial cables, such signal attenuation is acceptable for uses of the present invention. Furthermore, this loss may also be reduced by optimization of the hybrid catheter system design.

Figure 2A:
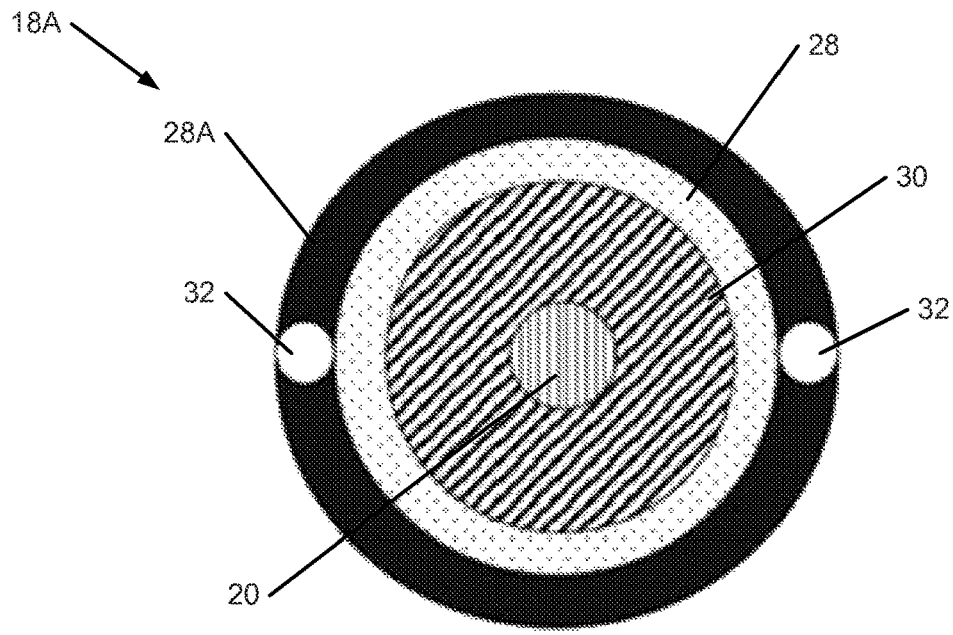
FIG. 2a is a front cross-sectional view of an optical fiber of an optoelectrical element for use with the hybrid catheter system of FIG. 1a or 1b.
Figure 2B:
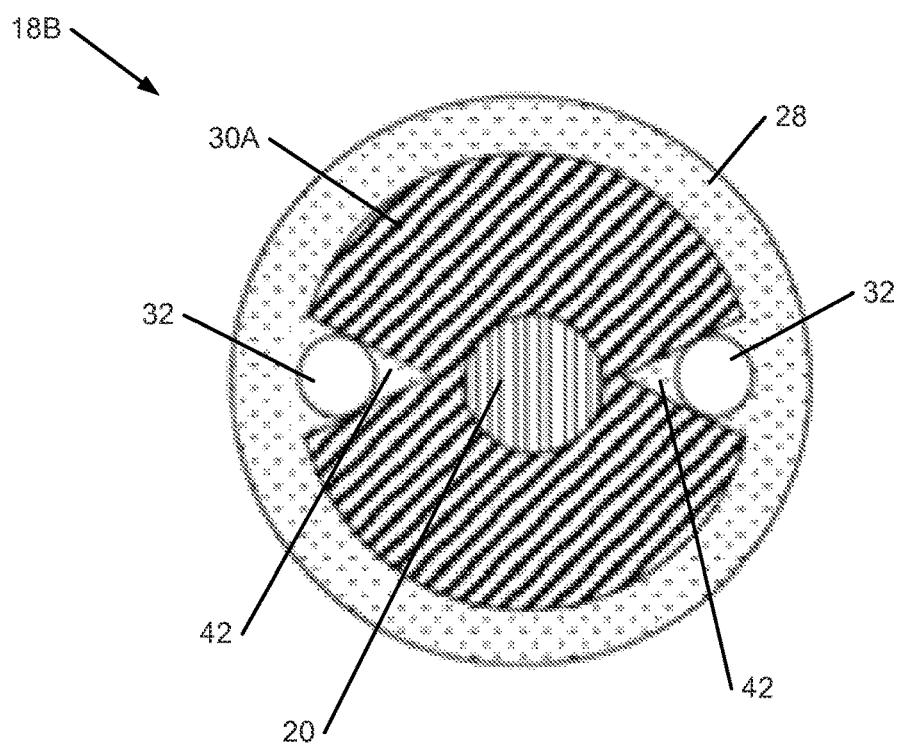
FIG. 2b is a front cross-sectional view of another optical fiber of an optoelectrical element for use with the hybrid catheter system of FIG. 1a or 1b.

Referring again to FIGS. 2a and 2b, examples of cross-sections of optical fibers 18A, 18B, respectively, of the optoelectrical element 12 of a single-shaft embodiment of the hybrid catheter 10 of the invention are illustrated. The single-shaft or single-strand nature of the structure of this embodiment enables the optoelectrical element 12 to operate as a substantially concentric single unit. FIG. 2a illustrates an embodiment of the optical fiber 18A with the core 20, cladding 30, a first coating 28, and a second optional flexible coating 28A. The two electrical connectors 32 can be embedded along the sides of the first coating 28 and the second coating 28A can be applied to cover the hybrid structure. FIG. 2b illustrates an embodiment of the optical fiber 18B with the core 20, a cladding 30A, and a single coating 28. In this arrangement, a custom uncoated optical fiber including two opposing grooves or troughs 42 in the cladding 30A can be used as the design base. An example uncoated fiber with opposing grooves is described in the U.S. Pat. No. 5,768,462, the entire contents of which are incorporated herein by reference. Using this base structure, the electrical connectors 32 can be laid or nested within the grooves 42 and the coating 28 can be applied to cover the hybrid structure and to embed the electrical connectors 32. In some embodiments, as shown in FIGS. 2a and 2b, the two electrical connectors 32 can be laid symmetrically along the optical fiber 18. In other embodiments, the two electrical connectors 32 can be laid asymmetrically along the optical fiber 18. For example, the optical fiber 18B can be designed with asymmetric grooves 42 in the cladding 30A, thus causing the nested electrical connectors 32 to be laid asymmetrically along the optical fiber 18B.

The above shaft designs of the present invention, where the electrical connectors 32 are juxtaposed with the optical fiber 18 by embedding them within the fiber coating 28, are advantageous over other known techniques of formatting the electrical connectors (such as, for example, metallization or internal electrode fibers). The metallization techniques often result in fragile shafts that crack easily. Additionally, standard metallization techniques offer uniform coverage of the fiber surface with a metallization material, while the structure of the electrode connectors in an embodiment of the present invention includes two individual electrodes isolated from one another. With respect to fibers with internal electrodes, such techniques have been extensively used for poling applications. To enable internal electrodes, fibers with two capillary holes in their claddings are manufactured, in which wires can be manually inserted. However, the manual insertion of wires is technically difficult and limited to fibers shorter than about 1 m. Instead of manually inserting the wires, molted metal can be drawn through the holes, which turns into electrical wires after solidification. This technique is also time consuming, requires special attention to prevent gaps in the deposited wires, and the mechanical stability of the resulting wires is unclear. Furthermore, connectorizing the electrodes requires side polishing the fiber and attaching external wires to the electrodes using conductive epoxy. In addition to the complexity of the process, the long-term stability of these contacts is unclear. In another technique, the wires may be inserted to the holes as the fiber are drawn, enabling the manufacture of long fibers with good mechanical properties. However, this technique also requires side-polishing to access the wires. It is further noted that such techniques based on fibers with capillary holes have only been developed for stationary optical devices and not for use in medical applications, where a higher degree of mechanical performance is required. In light of the above drawbacks of other techniques, advantages of the embedding method of the present invention include the simplicity of production and connectorization, and good mechanical properties of the catheter (for example, because it will not break when bent). The ability to connectorize easily is a result of laying the wires on the glass part of the fiber and under the coating. In addition, if the electrical connectors 32 are longer than the fiber 18, they will protrude naturally, in comparison to the above-described conventional techniques where they would need to be further pulled or otherwise formed.

In the hybrid catheter system 10, the natural protrusion of longer electrical connectors 32 can ease the electrical connections made between the electrical connectors 32 and the transducer 14, and the electrical connectors 32 and the rotary joint 40. More specifically, at the proximal end 24, the electrical connectors 32 can extend from the shaft and can be connected to the rotary joint 40. Also, as described above, the proximal end 24 of the optical fiber 18 can be connectorized and connected to the rotary joint 40. The rotary joint 40 can then connect the rotating shaft to the stationary portion 38, which may be connected to optical and electrical controls of the image system, as well as the image data processing system 35.

Figure 3:
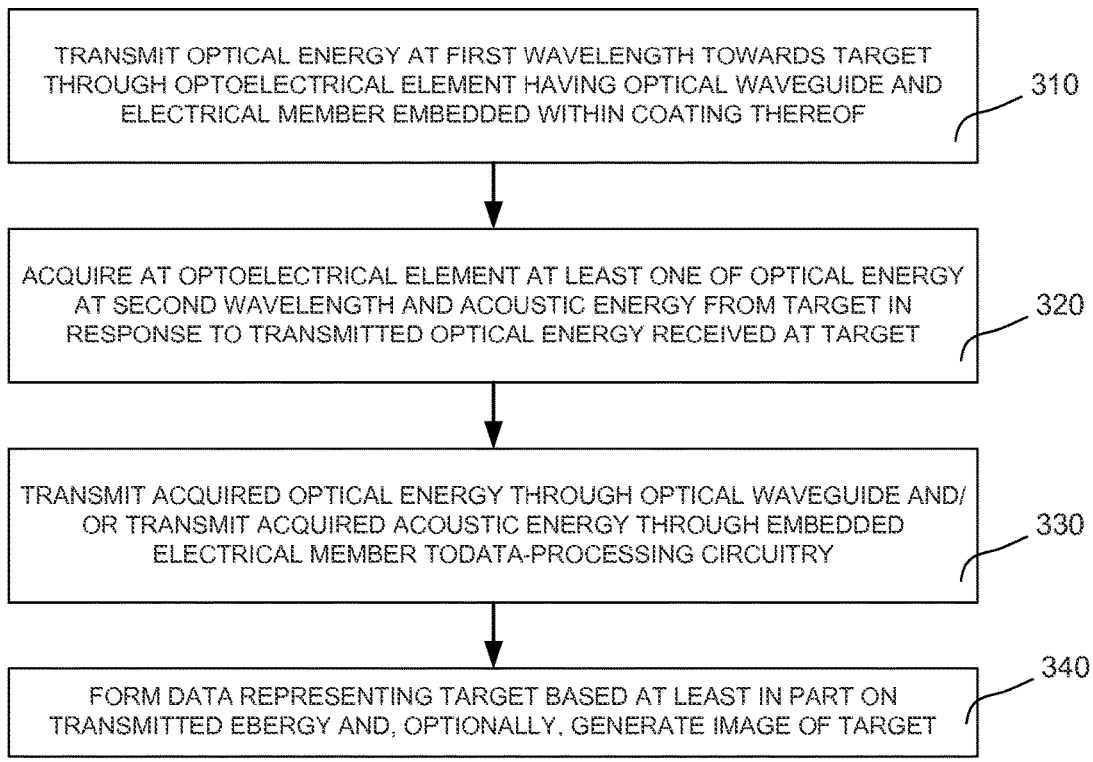
FIG. 3 is a flow-chart illustrating schematically an embodiment of the method of the invention.

An example of a method of the invention is schematically shown in a flow-chart of FIG. 3, wherein, at step 310, optical energy at a first wavelength is transmitted towards a target through an optoelectical element's distal end. The optoelectrical element includes an optical waveguide (such as an optical fiber) and an electrically-conductive member embedded in a coating layer thereof to electrically connect the proximal and distal ends of the optical waveguide. The target structure may include a lumen, with the optoelectrical element being judiciously dimensioned to fit inside such lumen. At step 320, a return generated by the target in response to being irradiated with the optical energy delivered through the optoelectric element is acquired, at the optoelectrical element, in a form of at least one of optical energy at a second wavelength and acoustic energy. The acquired return energy (whether the optical energy or the acoustic energy and/or both) is then transmitted, at step 330 through the optoelectrical element and its proximal end, to the data-processing circuitry such as, for example, a computer processor specifically programmed to form, at step 340, data representing the target and optionally to create an image of the target based at least in part on such formed data. The optional step of formation a target image may include generating a 3D image. In addition, the method may include a (not-shown in FIG. 3) at least one of steps of (i) determining at least one of functional and structural information about the target based on the data representing the target; (ii) transmitting an acoustic excitation signal towards the targer through the optoelectrical element; and (iii) acquiring acoustic energy from the target in response to the transmitted acoustic excitation signal received by the target.

References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. It is understood that in the drawings, the depicted structural elements are generally not to scale, and certain components may be enlarged relative to the other components for purposes of emphasis and clarity of understanding. It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, in the schematic logical flow chart diagram the depicted order and labeled steps of the logical flow are indicative of one embodiment of the presented method. Other steps and methods may be conceived that are equivalent in function, logic, or effect to one or more steps, or portions thereof, of the illustrated method.

The present invention has been described in terms of one or more preferred embodiments, and it should be appreciated that many equivalents, alternatives, variations, and modifications, aside from those expressly stated, are possible and within the scope of the invention.

What is claimed is:

1. A data-collecting system structured to obtain information about at least one portion of a target, the system comprising:
   an optoelectrical element including
      an optical fiber element having a core, a coating surrounding the core, an optical axis, a proximal end, and a distal end, the optical fiber element containing a multi-mode optical fiber structured to transmit light between the proximal and distal ends, and
      an electrical member embedded within the coating along the optical axis to electrically connect the proximal and distal ends;
   an optical coupling unit at the distal end; and
   a transducer disposed at the distal end and electrically connected to the electrical member, the transducer being operable
      to receive first energy, generated in response to excitation light that has been transmitted from the proximal end along said multi-mode optical fiber to the distal end and outcoupled from the distal end toward the target, and
      to convert the received first energy to an electrical signal to be transmitted along the electrical member,
   wherein the optical fiber element is configured to collect, through the optical coupling unit, fluorescent radiation generated at said at least one portion of the target in response to irradiation of said at least one portion with the excitation light through the optical coupling unit, said system being a catheter.

2. The system of claim 1, wherein the first energy is acoustic energy.

3. The system of claim 1, wherein the optical coupling unit is positioned between the distal end and the transducer, the optical coupling unit being rotatable about the optical axis.

4. The system of claim 3, wherein the optical coupling unit and the transducer are simultaneously rotatable about the optical axis.

5. The system of claim 1, wherein the target includes a lumen, and the optoelectrical element is configured as a single-shaft catheter dimensioned to be insertable into the lumen.

6. The system of claim 1, further comprising a light source optically coupled with the proximal end and configured to generate the excitation light, at a frequency sufficient to cause the target to generate the first energy, in response to being illuminated with the excitation light.

7. The system of claim 1, wherein the electrical member includes first and second wires embedded symmetrically about the optical axis.

8. The system of claim 1, further comprising an image data processing circuitry operably connected with the optoelectrical element through a rotary joint at the proximal end.

9. The system of claim 1, wherein the transducer is structured as an ultrasound transceiver.

10. The system of claim 1, wherein the optoelectrical element is equipped to outcouple light from the distal end in a direction that is transverse to the optical axis.

11. The system of claim 1, further comprising a rotary joint that is configured to enable a simultaneous rotation of the optoelectrical element and the transducer about the optical axis.

12. The system of claim 1, wherein the optoelectrical element is further configured to:
   a) transmit the light at a first wavelength toward the at least one portion of the target;
   b) acquire, from said at least one portion of the target, at least one of said fluorescent radiation and the first energy, in response to receiving the transmitted light at said at least one portion of the target; and
   c) effectuate at least one of (i) a transmission of the fluorescent radiation through the optical fiber and (ii) a transmission of the acquired first energy through the electrical member to an image data processing circuitry to form data representing said at least one portion of the target.

13. The system of claim 12, further configured to d) generate an image of the target using the acquired fluorescent radiation and the acquired first energy.

14. The system of claim 13, wherein the target includes a hollow lumen and wherein the system is further configured to perform steps a) through b) at angular intervals within the hollow lumen, and wherein step d) includes generating a circumferential, three-dimensional image of the hollow lumen.

15. The system of claim 12, further configured to determine at least one of functional and structural information about the target based on the data representing said at least one portion of the target.

16. The system of claim 15, further configured to generate a report about said at least one of functional and structural information.

17. The system of claim 12, further configured to convert the acquired first energy to an electrical signal.

18. The system of claim 12, further configured to:
   transmit an acoustic excitation signal toward said at least one portion of the target through said optoelectical element; and
   acquire the first energy from the target in response to the transmitted acoustic excitation signal having been received at said at least one portion of the target.

19. The system of claim 12, wherein the system is configured to transmit the light at a plurality of wavelengths.

* * * * *